United States Patent [19]

Batz et al.

[11] 4,423,227

[45] Dec. 27, 1983

[54] PROCESS FOR THE PREPARATION OF REACTIVE, COUPLABLE DERIVATIVES OF THE THYROID HORMONES

[75] Inventors: Hans-Georg Batz, Tutzing; Winfried Albert, Pähl; Helmut Lenz, Tutzing; Hans-Ralf Linke, Raisting; Fritz Stähler, Tutzing, all of Fed. Rep. of Germany

[73] Assignee: Boehringer Mannheim GmbH, Mannheim-Waldhof, Fed. Rep. of Germany

[21] Appl. No.: 307,141

[22] Filed: Sep. 30, 1981

[30] Foreign Application Priority Data

Oct. 7, 1980 [DE] Fed. Rep. of Germany ....... 3037858

[51] Int. Cl.$^3$ ............................................. C07F 7/10
[52] U.S. Cl. .................................... 548/406; 548/546; 556/410; 556/418; 556/419; 562/440; 562/447
[58] Field of Search ............... 556/418, 419, 424, 410; 562/440, 447; 548/406, 546

[56] References Cited

U.S. PATENT DOCUMENTS 2,889,364  6/1959  Anthony et al. .................... 562/447
3,046,306  7/1962  Meltzer et al. ..................... 562/447

OTHER PUBLICATIONS

Chemical Abstracts, 8th Coll. Index (1971).
Birkofer et al., Angewandte Chemie, vol. 77 (1965) pp. 414–426.

*Primary Examiner*—Richard Raymond
*Attorney, Agent, or Firm*—Felfe & Lynch

[57] ABSTRACT

Process for the preparation of reactive, couplable derivatives of the thyroid hormones 3,3′,5-triiodothyronine ($T_3$) and 3,3′,5,5′-tetraiodothyronine ($T_4$) by reaction with reactive carboxylic acid derivatives, which process comprises sylylating all the functional groups of the thyroid hormone by reaction with a reactive triorganosylyl derivative and then reacting the persylylated derivative of the thyroid hormone thus obtained with an activated carboxylic acid derivative.

11 Claims, 1 Drawing Figure

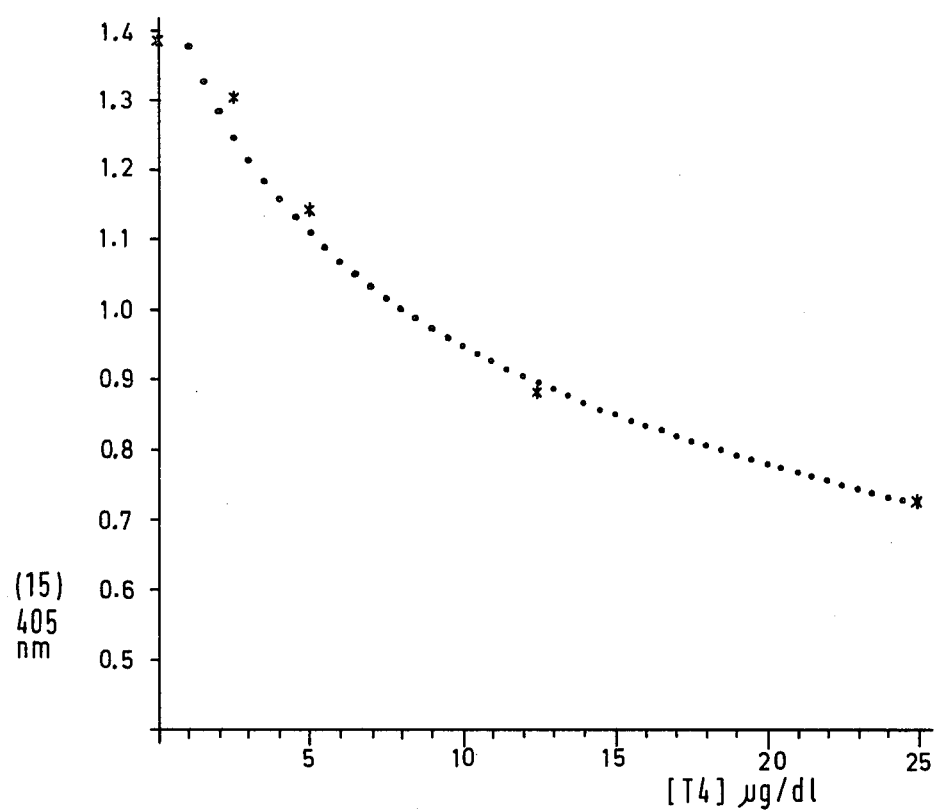

PROCESS FOR THE PREPARATION OF REACTIVE, COUPLABLE DERIVATIVES OF THE THYROID HORMONES

This invention relates to a process for the preparation of reactive, couplable derivatives of the thyroid hormones 3,3',5-triiodothyronine ($T_3$) and 3,3',5,5'-tetraiodothyronine ($T_4$). More specifically, the invention relates to such a process by reaction with reactive carboxylic derivatives. In further aspect, the invention relates to the use of such reactive couplable derivatives, e.g., for the preparation of insoluble derivatives by coupling with polymeric carriers or by copolymerization with unsaturated monomer.

The determination of the thyroid hormones $T_3$ and $T_4$ in serum is of considerable importance for clinical diagnosis. Usually, immunological processes are today used for the determination. Besides the radio-immunological processes, enzyme-immunological methods are today of increasing importance.

For the preparation of antibodies, the hormone ($T_3$, $T_4$), which immunologically is to be regarded as being a hapten, is first bound to a high molecular weight protein, for example albumin or polylysine, the actual antigen (immunogen) thus being obtained. In animals immunised therewith, there are formed antibody populations against these immunogens, including also specific antibodies against the hormone. These specific antibodies can be separated off by affinity chromatography by treating the antibody mixture with the hormone covalently bound to a carrier material.

Besides the radio-immunological detection with radio-active marked hormone, enzyme-immunological detection is of increasing importance. The enzyme or the reaction catalysed by it here serves as the basis of the detection method, the hormone having to be covalently bound to the enzyme.

As follows from the described use, there is a need for derivatives of thyroid hormones $T_3$ and $T_4$ which have a specifically reacting functional group which, under very mild conditions (pH value of from 6 to 8, ambient temperature) can react with functional groups of, in particular, proteins, such as enzymes. The functional groups on the proteins are, in particular, the $NH_2$ and SH groups. A series of specific and mild reacting substances is here known to the expert. Thus, the amino group already reacts at a pH value of 7 to 8 with reactive esters, imidoesters or glutardialdehyde. Haloacetyl radicals, especially the iodoacetyl radical, and the maleinimido radical, in particular, react specifically with SH groups.

The introduction of such specifically and sensitively reacting groups into other molecules gives rise to difficulties in the case of the thyroid hormones $T_3$ and $T_4$ since these are insoluble in most conventional solvents. Dissolving is only possible in aqueous alkaline solution in which other sensitively reacting groups are again hydrolysed. These difficulties are usually avoided by using, instead of the free thyroid hormones $T_3$ or $T_4$, appropriate derivatives protected on the amino or carboxyl group and via which the still free second function is then activated and coupled. Splitting off of the protective group is usually omitted since, in this case, undesired side reactions can be expected.

This problem is very clear in the case of the maleinimide derivative of the hormone $T_3$ or $T_4$ for the SH-specific coupling on to galactosidase. Federal Republic of Germany Patent Specification No. 26 56 155 describes the preparation of o-maleinimidobenzoyl-$T_3$. When attempting to prepare measurable amounts of this derivative, it was only possible to obtain yields of less than 5% since the thyroid hormone $T_3$ is almost insoluble in the solution and the maleinimido compound, as the second reaction component, is already completely hydrolysed after only a few hours of reaction time, reference thereto also being made in this German Patent Specification. Reference to this instability has also been made by E. Ishikawa et al. ("Enzyme labelled immunoassay of hormones and drugs", 1978, pub. Walter de Gruyter & Co., Berlin/New York). According to them, the N-alkylmaleinimido derivatives are substantially more stable than the N-benzoyl derivatives. However, even when using such more stable derivatives, for example 6-maleinimidocaproic acid, the corresponding derivative of the thyroid hormone $T_4$ could only be obtained in a yield of less than 5% (see O. Keller and J. Rudiger, Helv. Chim. Acta, 58, 531–541/1975).

Certainly because of these difficulties, it has also already been suggested to prepare the m-maleinimidobenzoyl derivative of $T_4$ methyl ester instead of the free thyroid hormone $T_4$ (see N. Monji et al., BBRC, 85, 671–677/1978). However, a saponification of the ester is then not carried out.

It is an object of the present invention to provide the expensive thyroid hormones $T_3$ and $T_4$, in substantially better yields than was previously possible, with reactive groups which then permit coupling with a polymeric carrier, for example a protein and especially a high molecular weight protein.

Thus, according to the present invention, there is provided a process for the preparation of reactive, couplable derivatives of the thyroid hormones 3,3',5-triiodothyronine ($T_3$) and 3,3',5,5'-tetraiodothyronine ($T_4$) by reaction with reactive carboxylic acid derivatives, wherein all the functional groups of the thyroid hormone are silylated by reaction with a reactive triorganosilyl derivative and the persilylated derivative of the thyroid hormone thus obtained is reacted with an activated carboxylic acid derivative.

The products obtained by the use of the process according to the present invention can be coupled to polymeric carriers, especially proteins, more especially enzymes and particularly β-galactosidase, and can also be copolymerised with unsaturated monomers.

The feature of the process according to the present invention which is of especial importance is the persilylation of the thyroid hormones $T_3$ and $T_4$ in which all of the functional groups are reacted with the silylation agent, the result of which is that this intermediate product is soluble in many organic solvents and an intermediate product is obtained which can readily be reacted under mild conditions with reactive carboxylic acid derivatives, for example acid chlorides, acid anhydrides and reactive esters.

It is already known that amino acids, after complete silylation, can be reacted very easily with reactive carboxylic acid derivatives (see L. Birkhofer et al., Angewandte Chemie, 77, 414–426/1965). However, this process has not proved to be useful in peptide syntheses since the trimethylsilyl group usually employed is very sensitive to hydrolysis and is even split off by the action of methanol. However, according to the present invention, it has been shown that this reactivity is of great advantage since, in the case of the splitting off of the silyl group and especially of the trimethylsilyl group, other sensitive groups, for example the maleinimido radical, are not attacked.

Surprisingly, we have thereby found that the persilylated thyroid hormones $T_3$ and $T_4$ formed as intermediate products in the process according to the present invention can be reacted much more easily and with better yields than the corresponding analogous simple amino acid, i.e. tyrosine.

Thus, according to the process of the present invention, all the functional groups of the thyroid hormones $T_3$ (3,3′,5-triiodothyronine) and $T_4$ (3,3′,5,5′-tetraiodothyronine) are silylated by reaction with a reactive triorganosilyl derivative and the persilylated derivative obtained is then reacted with an activated carboxylic acid derivative.

According to a preferred embodiment of the process of the present invention, the triorganosilyl derivative used is a reactive trialkylsilyl derivative, such as hexamethyldisilazane, trimethylchlorosilane, N-trimethylsilylacetamide and/or triethylaminosilane.

The persilylation is preferably carried out with the use of an equimolar or excess amount of the silylation agent. It is thereby possible to work in the presence of an organic solvent which is inert under the reaction conditions, for example a polar organic solvent which does not contain any hydroxyl groups or nucleophilic substituents, which can themselves be silylated. Examples of such solvents include aromatic hydrocarbons, such as benzene, toluene, xylene and the like. The reaction can also be carried out in the presence of a catalyst and/or of an acceptor for the acid formed in the course of the reaction, for example in the presence of sulphuric acid when using hexamethyldisilazane or in the presence of triethylamine when using trimethylchlorosilane. The reaction can be carried out at a temperature of from ambient temperature up to the boiling temperature of the reaction mixture or of the solvent.

In the case of this silylation reaction, the amino groups, the hydroxyl groups and the carboxyl groups are silylated, the result of which is that the hydroxyl groups and the carboxyl groups are protected, whereas the amino group of the reacted thyroid hormone $T_3$ or $T_4$ is activated and is thus available for reaction with an activated carboxylic acid derivative, such as an acid chloride, an acid anhydride or a reactive ester.

In the second step of the process according to the present invention, the persilylated derivative of the thyroid hormone is reacted with an activated carboxylic acid derivative, i.e. a bifunctional carboxylic acid derivative which is activated on the carboxyl group. Activated carboxylic acid derivatives which can be used for this purpose include reactive esters, imido esters, reactive acid chlorides and acid anhydrides. Of the reactive esters and imido esters, the hydroxysuccinimide esters are preferred. Activated carboxylic acid derivatives which are especially preferred according to the present invention include acryloyl chloride, acrylic acid imidomethyl ester, iodoacetyl-p-nitrophenyl ester, bromoacetyl hydroxysuccinimide ester, derivatives of carbobenzoxy-γ-aminobutyric acid, carbobenzoxy-β-aminopropionic acid (which, after splitting off of the carbobenzoxy radical, contains the amino group as the second functional group) and/or 6-maleinimido-hexanoic acid N-hydroxysuccinimide ester. Further examples of reactive carboxylic acid derivatives which can be used according to the present invention are given, for example, in Federal Republic of Germany Patent Specifications Nos. 26 31 656 and 22 37 083, for example ethylene glycol bis-propionic acid bis-hydroxysuccinimide ester, oxy-bis-propionic acid hydroxysuccinimide ester, oxysuccinimido-glutaric acid aminoacetaldehyde dimethylacetal, methacryloyl-hydroxycarboxylic acid oxysuccinimide ester, hydroxysuccinimido-N-2-hydroxyethyl-N′,N′-dimethylurea succinic acid ester, acrylic acid hydroxysuccinimide ester, methacrylic acid hydroxysuccinimide ester, acrylic acid hydroxybenzotriazole ester, methacrylic acid hydroxybenzotriazole ester, acrylic acid 2,4,5-trichlorophenyl ester, methacrylic acid 2,4,5-trichlorophenyl ester, N-vinylcarbamic acid hydroxysuccinimide ester, N-vinylcarbamic acid 1-hydroxy-benzotriazole ester, N-vinylcarbamic acid 2,4,5-trichlorophenyl ester and polymers and copolymers based upon these unsaturated esters.

After coupling with the reactive carboxylic acid derivative, there is obtained a $T_3$ or $T_4$ compound which is silylated on the —OH and —COOH. In order to isolate the $T_3$ or $T_4$ compound, the silylated compound is directly used for the reaction with a protein since the hydrolysis is spontaneously formed an addition to the aqueous solution. The silyl groups are hereby split off by the aqueous medium. Whereupon the reaction of the active groups, in the case of the maleinimido and haloacetyl radicals, leads to a coupling with an SH group, in the case of the bis-carboxylic acid and aldehyde carboxylic acid to a coupling with $NH_2$ groups and in the case of aminobutyric acid to a coupling with COOH groups.

Therefore, the present invention is also concerned with the use of the reactive couplable derivatives of the thyroid hormones $T_3$ and $T_4$ prepared in this manner for the preparation of coupling products of these thyroid hormones with polymeric carriers, especially proteins and particularly enzymatically active proteins. Because of the mild reaction possible with the use of these reactive, couplable derivatives of the said thyroid hormones, this method can also be used for coupling these thyroid hormones on to enzymatically-active proteins which can then be used in the scope of an ELISA test. β-Galactosidase is especially suitable because of the relatively high number of SH groups which it contains, not all of which are necessary for the enzymatic activity.

The following Examples are given for the purpose of illustrating the present invention. These Examples are concerned with the preparation according to the present invention of reactive, couplable derivatives via trimethylsilylated intermediate products. Besides a comparison of the reactions with the thyroid hormone $T_4$ and the analogous simple amino acid tyrosine, there is also investigated and compared the reaction of various activated carboxyl derivatives with tris-trimethylsilyl derivatives of the thyroid hormone $T_4$. According to this, the reactive chlorides are superior to the reactive esters. Thus, N-propionyltyrosine could only be prepared via propionyl chloride but not via propionic acid p-nitrophenyl ester or propionic acid hydroxysuccinimide ester. With propionic acid imidomethyl ester there correspondingly resulted the amidinium compound.

Since the tris-trimethylsilyl derivative of the thyroid hormone $T_4$ can be better reacted than the tris-trimethylsilyl derivative of tyrosine, the reaction with propionic acid hydroxysuccinimide ester here takes place with good yields. The reaction with propionic acid p-nitrophenyl ester takes place much more poorly.

As reactive couplable derivatives of the thyroid hormones $T_3$ and $T_4$ there were prepared, according to the present invention: N-acryloylthyroxine, N- bromoacetylthyroxine, carbobenzoxy-γ-aminobutyric acid thyroxine, N-(6-maleinimidohexanoyl)-thyroxine and N-(6-maleinimidohexanoyl)-T$_3$.

EXAMPLE 1

Preparation of the silylated intermediate product

A. Silylated thyroid hormone T$_4$ (silylated thyroxine)

The sodium salt of thyroxine is dried for 12 hours over phosphorus pentoxide at oil pump vacuum. 799 mg. (1 mMol) of the dried thyroxine sodium salt are then boiled under reflux with 30 ml. anhydrous chloroform, 550 mg. (0.68 ml.) trimethylchlorosilane and 505 mg. (0.70 ml., 5 mMol) triethylamine for 1.5 to 2 hours, with the exclusion of light, a completely clear, pale yellowish solution being obtained.

The silylated thyroxine prepared in this manner is immediately further worked up and, as far as possible, protected against light.

B. Silylated thyroid hormone T$_3$

The procedure described above under A. is repeated with the use of 673 mg. 3,3',5-triiodothyronine instead of thyroxine.

C. Silylated tyrosine

L-tyrosine is dried for 12 hours over phosphorus pentoxide at oil pump vacuum. 1.81 g. (10 mMol) of this dried amino acid, 3.25 g. (4.0 ml., 30 mMol) trimethylchlorosilane and 3.03 g. (4.2 ml., 30 mMol) triethylamine are then boiled under reflux in 50 ml. anhydrous chloroform for 1 hour. After only a few minutes, the solution begins to become clear. The product obtained is immediately further worked up.

EXAMPLE 2

N-Propionyltyrosine 10 mMol silylated tyrosine (Example 1, C) is allowed to react for 20 hours at 20° C. with 0.925 g. (10 mMol) propionyl chloride, then hydrolysed with 5 ml. methanol and concentrated several times with the addition each time of methanol. The material thus obtained is chromatographed with ethyl acetate over 500 ml. silica gel (60). Yield 1.37 g. (57% of theory).

Elementary analysis: calculated: C 60.8%; H 6.37%; N 5.9%; found: 61.8%; 6.6%; 5.47%

NMR spectrum (in DDMSO):=0.94 (t, CH$_3$), 6.83 (qu. $^{CH}$phenol).

EXAMPLE 3

N-Propionyltyrosine

The procedure of Example 2 is repeated but with the use of propionic acid hydroxysuccinimide ester instead of propionyl chloride. The desired product is obtained in a yield of 8%.

EXAMPLE 4

N-Propionyltyrosine

The procedure of Example 2 is repeated but with the use of propionic acid p-nitrophenyl ester instead of propionyl chloride. The desired product is obtained in a yield of 5%.

EXAMPLE 5

Propionylimidotyrosine

The procedure of Example 2 is repeated but with the use of propionic acid imidomethyl ester instead of propionyl chloride, 1.1 g. (46% of theory) of chromatographically pure propionylimidotyrosine (amidine) being obtained in the form of a yellowish oil.

R$_f$-value: 0.42 (SiF plate, elution agent: ethyl acetate/benzene/glacial acetic acid/water mixture 10/10/2/1 v/v/v/v).

EXAMPLE 6

N-Propionylthyroxine 0.5 mMol Thyroxine is stirred overnight at ambient temperature with 1.71 mg. (1 mMol) propionic acid hydroxysuccinimide ester and then hydrolysed with 1 ml. methanol and finally with water. The resultant solution is evaporated, dried and extracted with 40 ml. chloroform. The extract is again evaporated, extracted with acetone and the residue of the acetone extract recrystallised twice from a methanol/water mixture. Yield: 188 mg. (45% of theory) N-propionylthyroxine.

Elementary analysis: calculated: C 25.9%; H 1.81%; N 1.68%; found: 25.5%; 1.65%; 1.60%

NMR spectrum (DDMSO):=0.94 (t, CH$_3$), 7.06 (s, $^{CH}$phenylene), 7.8 (s, $^{CH}$phenol).

EXAMPLE 7

N-Propionylthyroxine

The procedure of Example 6 is repeated but, instead of propionic acid hydroxysuccinimide ester, there is used propionic acid p-nitrophenyl ester, N-propionylthyroxine being obtained in a yield of 12% of theory.

EXAMPLE 8

N-Acryloylthyroxine 2 mMol Silylated thyroxine (see Example 1, A) and 190 mg. (2 mMol) freshly distilled acryloyl chloride are stirred for 24 hours at ambient temperature, then hydrolysed with 5 ml. methanol, evaporated, treated several times with methanol and again evaporated. The residue is taken up in ethyl acetate and purified chromatographically over a column of 250 ml. silica gel (60), 130 mg. (16% of theory) N-acryloylthyroxine being obtained.

Elementary analysis: calculated: C 26.0%; H 1.58%; N 1.69%; found: 27.7%; 1.88%; 1.56%

NMR spectrum (DDMSO):=5.7 (qu, CH=), 6.93 (s, $^{CH}$phenylene), 7.68 (s, $^{CH}$phenol).

EXAMPLE 9

N-Bromoacetylthyroxine

This compound is prepared according to the method described in Example 8, using bromoacetyl hydroxysuccinimide ester instead of acryloyl chloride.

EXAMPLE 10

N-Maleinimidohexanoylthyroxine 3.13 g. (1 mMol) 6-Maleinimidohexanoic acid N-hydroxysuccinimide ester are added to 1 mMol silylated thyroxine (see Example 1, A) in 40 ml. anhydrous chloroform and the reaction mixture stirred for 16 hours at a bath temperature of 60° C. The reaction mixture is subsequently allowed to cool, 2.0 ml. methanol are added thereto and the mixture is then further stirred for 30 minutes at ambient temperature. The reaction mixture is rapidly shaken with 20 ml. water and 1 ml. concentrated acetic acid and then again shaken twice with 20 ml. amounts of water. The solution is dried with anhydrous sodium sulphate and filtered and the filter cake is again extracted with 30 ml. chloroform. The combined chloroform extracts are evaporated and the desired product crystallised out from the oily residue overnight at 4° C. and then dried in a vacuum, 300 mg. (30% of theory) N-maleinimidohexanoylthyroxine being obtained.

Elementary analysis: calculated: C 31.3%; H 2.29%; N 2.97%; I 52.8%; found: 30.6%; 2.19%; 3.7%; 50.5%

NMR spectrum (DDMSO):=7.0 (s, $^{CH}$=maleic), 7.06 (s, $^{CH}$phenylene), 7.80 (s, $^{CH}$phenol).

EXAMPLE 11

M-Maleinimidohexanoyl-3,3',5-triiodothyronine

The procedure of Example 10 is repeated but using silylated 3,3',5-triiodothyronine ($T_3$) instead of silylated thyroxine, 377 mg. (32.8% of theory) N-maleinimidohexanoyl-3,3',5-triiodothyronine being obtained.

EXAMPLE 12 (EXAMPLE OF USE)

Determination of hyroxine in human serum using β-galactosidase-(6-maleinimidohexanoyl)-thyroxine N-Maleinimidohexanoylthyroxine, obtained according to Example 10, is coupled in aqueous solution with β-galactosidase. The coupling product is, as described hereinafter, used for the determination of thyroxine by the ELISA method:

Reagents: 0.01 ml. highly affine rabbit antithyroxine antiserum, the dilution of which was determined by titration with the $T_4$-galactosidase conjugate; 0.02 ml. β-galactoside-6-maleinimidohexanoylthyroxine conjugate in a dilution which, without the addition of unmarked thyroxine, gave an extinction in the test system of substantially 1.0 A in 15 minutes at a wavelength of 405 nm.; 0.02 ml. thyroxine standard in the human sera, the concentration of which varied between 0 and 25 μg./100 ml.;

0.23 ml. assay buffer (0.016 M barbiturate buffer, pH 8.6, containing 0.04% "Tween" 20).

The conjugate and the antiserum dilutions were prepared with assay buffer. The above reagents were pipetted together into a vessel and incubated for 10 minutes at 22° C. In this time, the marked and the unmarked forms of the thyroxine competed for the binding places on the antithyroxine antiserum.

The separation of the antibody-bound and of the free $T_4$-β-galactosidase conjugate took place on an immune adsorbent, consisting of a "Sepharose"-4B column, coupled with rabbit antithyroxine antibodies (volume 1 ml.). The mixture was applied to the column and eluted with 2 ml. of assay buffer.

The eluate was mixed with 0.5 ml. substrate solution (0.1 M sodium chloride, 0.01 M magnesium chloride, 0.1 M mercaptoethanol, 0.05 g./100 ml. sodium azide and 25 mM o-nitrophenyl β-D-galactoside) and the extinction measured photometrically at a wavelength of 405 nm. after the expiry of an enzyme reaction time of 15 minutes.

| concentration of unmarked $T_4$ | 0 | 2.5 | 5 | 12.5 | 25 g./dl. |
|---|---|---|---|---|---|
| extinction (15) of column eluate | 1.38 | 1.30 | 1.14 | 0.88 | 0.73 |

The dependency of the measurement signal of the unmarked $T_4$ concentration can be expressed in the form of a reference curve, which is given in FIG. 1 of the accompanying drawing.

It will be understood that the specification and examples are illustrative but not limitative of the present invention and that other embodiments within the spirit and scope of the invention will suggest themselves to those skilled in the art.

What is claimed is:

1. Process for the preparation of reactive, couplable derivatives of the thyroid hormones 3,3',5-triiodothyronine ($T_3$) and 3,3',5,5'-tetraiodothyronine ($T_4$) by reaction with reactive carboxylic acid derivatives, which process comprises sylylating all the functional groups of the thyroid hormone by reaction with a reactive triorganosylyl derivative and then reacting the persylylated derivative of the thyroid hormone thus obtained with an activated carboxylic acid derivative.

2. Process as claimed in claim 1 wherein the triorganosylyl derivative used is a reactive trialkylsylyl derivative.

3. Process as claimed in claim 2, wherein the reactive trialkylsylyl derivative is hexamethyldisilazane, trimethylchlorosilane, N-trimethylsylylacetamide and/or triethylaminosilane.

4. Process as claimed in claim 1, wherein the persylylation is carried out with the use of an equimolar or excess amount of the sylylation agent in the presence of an organic solvent which is inert under the reaction conditions and optionally of a catalyst at a temperature of from ambient temperature to the boiling temperature of the solvent.

5. Process as claimed in claim 1, wherein the activated carboxylic acid derivative is a bifunctional carboxylic acid derivative activated on the carboxylic group.

6. Process as claimed in claim 5, wherein the activated carboxylic acid derivative is a reactive ester, an imido ester, a reactive acid chloride or an acid anhydride.

7. Process as claimed in claim 6, wherein the activated carboxylic acid derivative is propionyl chloride.

8. Process as claimed in claim 6, wherein the activated carboxylic acid derivative is acryloyl chloride.

9. Process as claimed in claim 6, wherein the activated carboxylic acid derivative is bromoacetyl hydroxysuccinimide ester.

10. Process as claimed in claim 6, wherein the activated carboxylic acid derivative is 6-maleinimidohexanoic acid N-hydroxysuccinimide ester.

11. Process as claimed in claim 1, wherein more than 1 activated carboxylic acid derivative is used.

* * * * *